(12) United States Patent
Godin

(10) Patent No.: US 7,537,774 B2
(45) Date of Patent: May 26, 2009

(54) THERAPEUTIC FORMULATION

(75) Inventor: Jerome Godin, Hialeah, FL (US)

(73) Assignee: Orion Therapeautics, LLC, Troy, MI (US)

( * ) Notice: Subject to any disclaimer, the term of this patent is extended or adjusted under 35 U.S.C. 154(b) by 0 days.

(21) Appl. No.: 11/317,534

(22) Filed: Dec. 23, 2005

(65) Prior Publication Data

US 2007/0149623 A1 Jun. 28, 2007

(51) Int. Cl.
*A61K 9/00* (2006.01)
*A61K 31/13* (2006.01)
*A61K 31/05* (2006.01)
*A01N 31/08* (2006.01)
*A01N 35/00* (2006.01)

(52) U.S. Cl. .................. 424/400; 514/690; 514/731
(58) Field of Classification Search .............. 424/1; 514/731; 524/690, 731
See application file for complete search history.

(56) References Cited

U.S. PATENT DOCUMENTS

| | | | |
|---|---|---|---|
| 2,875,769 A * | 3/1959 | Rosmarin et al. ........... 132/208 |
| 4,283,342 A | 8/1981 | Yolles |
| 4,447,608 A | 5/1984 | Jones et al. |
| 4,564,616 A | 1/1986 | Jones et al. |
| 4,950,750 A | 8/1990 | Ogawa et al. |
| 4,973,674 A | 11/1990 | Brasca et al. |
| 5,157,049 A | 10/1992 | Haugwitz et al. |
| 5,229,419 A * | 7/1993 | McLaughlin et al. ........ 514/473 |
| 5,563,143 A | 10/1996 | Cohan et al. |
| 5,691,373 A | 11/1997 | Berryman et al. |
| 5,814,319 A | 9/1998 | Nakano |
| 5,977,141 A | 11/1999 | Ortwine et al. |
| 6,207,648 B1 | 3/2001 | Waxman et al. |
| 6,255,291 B1 | 7/2001 | Germano |
| 6,555,677 B2 | 4/2003 | Petrillo et al. |
| 6,576,660 B1 * | 6/2003 | Liao et al. .................... 514/456 |
| 6,809,176 B2 | 10/2004 | Blokhin et al. |
| 6,888,014 B2 | 5/2005 | Huang et al. |

FOREIGN PATENT DOCUMENTS

EP 499467 A2 * 8/1992

OTHER PUBLICATIONS

Shukla, Y.; Pal, S.; "Complementary and Alternative Cancer Therapies: Past, Present and Future Scenario", Jan.-Mar. 2004, Asian Pacific Journal of Cancer Prevention, vol. 5(1), 3-14.*

* cited by examiner

*Primary Examiner*—Sreeni Padmanabhan
*Assistant Examiner*—Kendra D Carter
(74) *Attorney, Agent, or Firm*—Butzel Long

(57) ABSTRACT

A pharmaceutical composition including a salt of rhodizonic acid, an OH anion-generating base, a non-toxic acid, a quinone, a salt-containing sulfite, catechol and, optionally, an acetogenin. The formulation demonstrates positive effects against cancer, autoimmune disease, viruses and provides antioxidant protection against peroxyl, hydroxyl and super oxide radicals.

6 Claims, 4 Drawing Sheets

| Material | Peroxy | Hydroxyl | Superoxide | |
|---|---|---|---|---|
| Vitamin E: 400 IU | 75 | 1125 | 32 | 1125 capsules |
| Vitamin C: 8 oz glass OJ | 2550 | * | * | 2550 glasses |
| Brocolli: Raw portion | 11 | 628 | 11 | 628 portions |
| α-Lipoic acid | 249 | 148 | 13 | 249 capsules |
| Grapeseed: 60 mg | 3 | 307 | 43 | 307 capsules |
| Green Tea Extract | 15 | 8 | 15 | 15 capsules |

FIG. 1

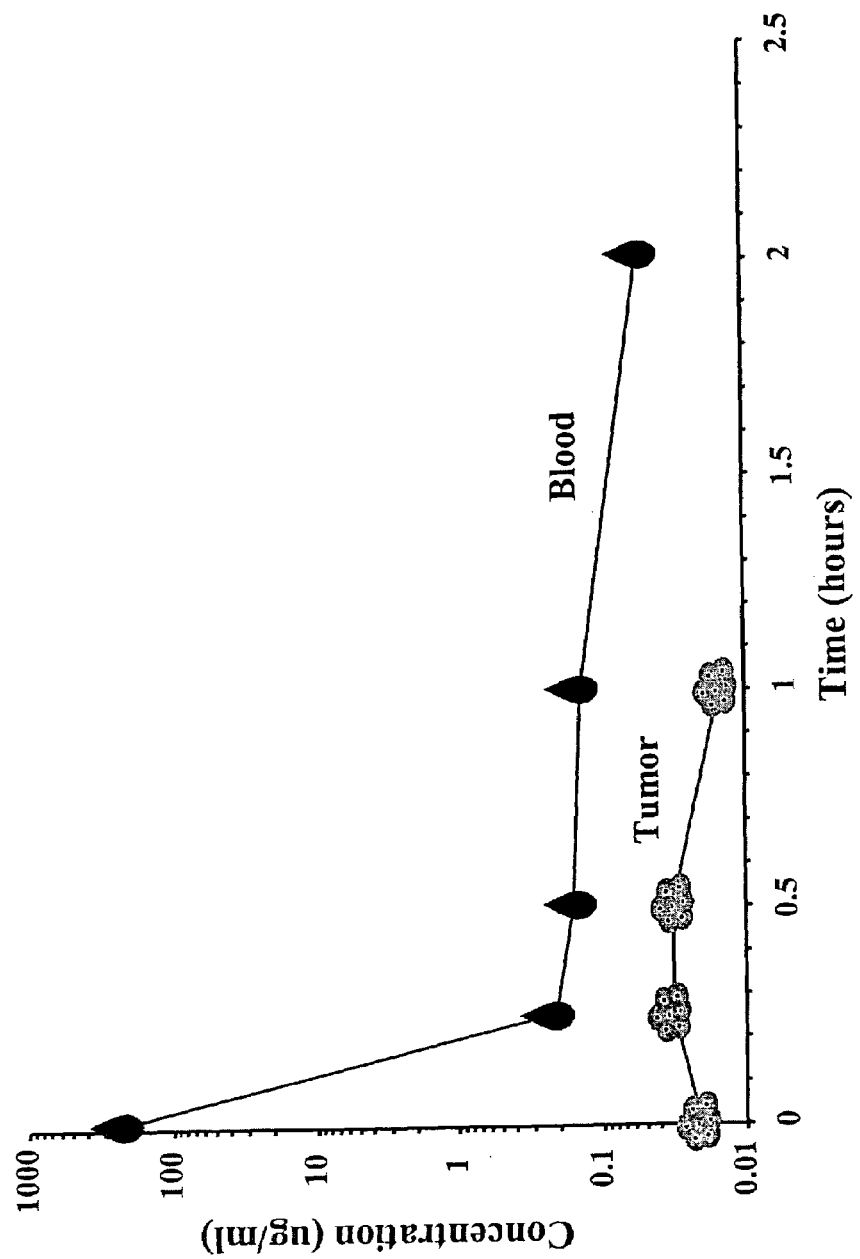

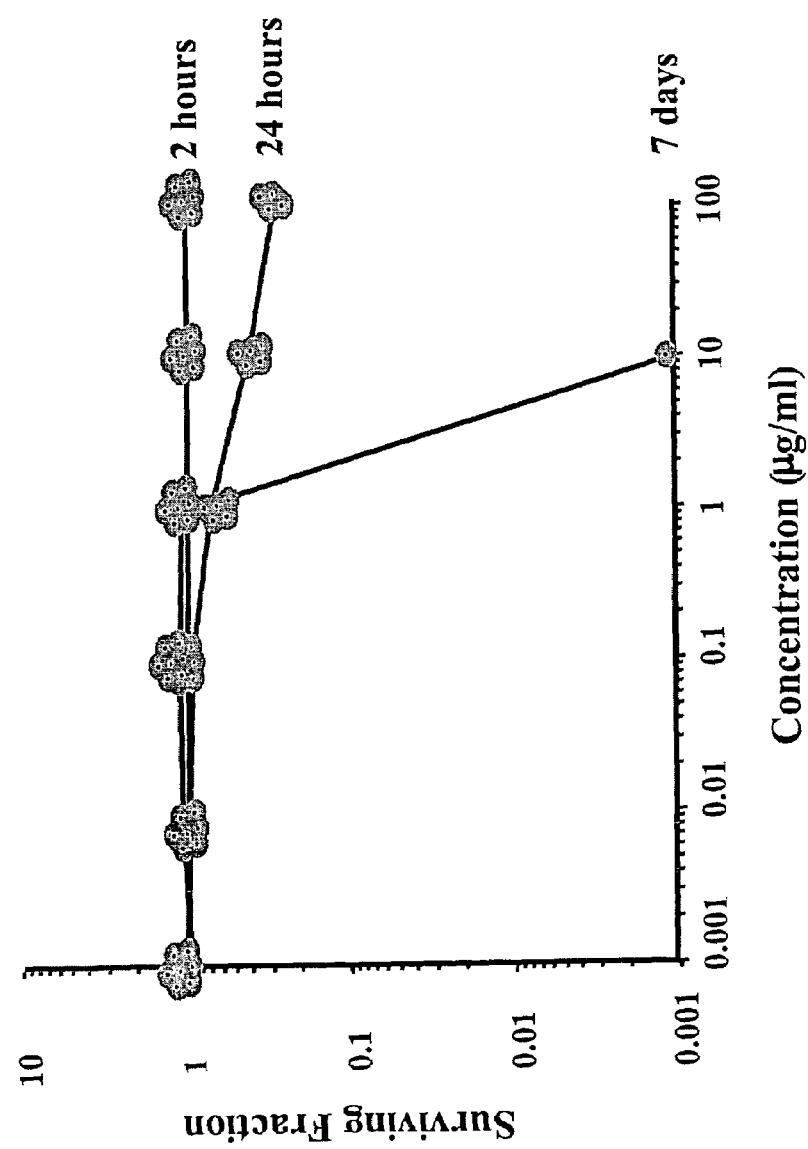

THERAPEUTIC FORMULATION

BACKGROUND AND SUMMARY OF THE INVENTION

I. Field of the Invention

The present invention generally relates to a therapeutic composition. More particularly, the present invention relates to a pharmaceutical, nutraceutical, or nutratherapeutical formulation that includes antioxidants. The formulation demonstrates positive effects against cancer, autoimmune disease, viruses and provides antioxidant protection against peroxyl, hydroxyl and super oxide radicals.

II. Description of the Relevant Art

It is well known that free radicals are chemically reactive molecules that damage cellular structure and function. Free radicals are oxidants that damage and destroy healthy cells. Oxygen-based free radicals include peroxyls (ROO—), superoxides ($O_2$—) and hydroxyls (—OH). Sources of free radicals include ultraviolet radiation, carcinogens, and high-fat processed foods. It is also known that physical stress and even normal cell function in the production of energy are both sources for the creation and release of free radicals. A broad variety of disease states have been linked to the presence of free radicals, including arthritis, cancer, heart dysfunction, atherosclerosis, hyperoxia, stroke, cataractogenesis, retinal damage, liver injury, sexual dysfunction, periodontis, vasospasms, dermatitis, and asthma.

In response to the overwhelming presence of oxygen-based free radicals in our natural environment, attention has focused on antioxidants, compounds that can inhibit the cellular damage caused by free radicals. Natural sources of antioxidants are known and include vitamins C and E, broccoli, alpha-Lipoic acid, grapeseed, and green tea extract. While offering an avenue to obtaining the positive effects of antioxidants, the dosages of these natural foods needed to offset the oxidants is extremely high.

Attempts have been made to provide concentrated antioxidants as a pharmaceutical, a nutraceutical, or a nutratherapeutical according to various formulations. Each of these formulations included tetrahydroxy-1,4-quinone ($C_6H_4O_6$) (hereinafter referred to occasionally as "THQ") (in its free form and its sulfited form), croconic acid (in its free form and its sulfited form), and catechol as active ingredients. These formulations have gone by various names, including "Entelev®," "Cantron®" (in three versions), "Cancell®," and "Protocel®" (in three versions). Perhaps the best known of these early attempts at providing an effective anti-cancer, anti-viral formulation is the "Cantron®" composition which had, in addition to catechol, varied amounts of croconic acid (in its free form and its disulfited form), THQ (in its free form and its sulfited form) and rhodozonic acid, the latter converting in part to croconic acid (in its free form and its disulfited form) during the formulation process. Various additional ingredients to these formulations include copper, potassium, triquinoyl, leuconic acid, and traces of inositol.

While providing some improvement in the state of the art, these formulations have not proven either fully effective or completely desirable. These shortcomings include unmanageable and inadequate dosing requirements, undesirable physical characteristics of the composition, and safety issues related to the manufacturing process.

Dosage management has been a problem with these compositions in that the liquid of known formulations needs to be four to five times per day. This is an extremely difficult schedule to follow even under the best of circumstances. The problem is further compounded by the difficulty of traveling with these compositions which is bulky. The container top is subject to loosening because of the gases naturally generated by the composition.

The physical characteristics of known formulations also make use of these compositions problematic. Specifically, the known compositions are designed to be orally ingested. However, the oral liquid has an extremely foul metallic taste. Users historically found the composition unappetizing, this problem being compounded by the user's need to consume the composition four or five times daily. Beyond taste, the dark black liquid of known compositions is itself visually unappealing. The color of the known compositions is known to stain teeth, clothing, furniture, and carpeting.

Of concern to manufacturers is the production process itself. The manufacturing procedure of the formula is extremely dangerous as the oxidation process to create the various compounds causes the release of a highly toxic and acidic gas. The manufacturing method of known compositions also causes the release of hazardous nitrous peroxides into the atmosphere, causing pollution and possible ozone damage. Experience has taught that the larger the volume of product being produced, the more dangerous the chemical reaction. So dangerous is the manufacturing procedure for known compositions that production on a large scale may lead to injury or death, which is the reason that previous manufacturing has been done on a small scale only. Because of the level of pernicious nitric fumes generated, even protective wear that would ordinarily be effective (such as gas masks) fail to protect the operator. Furthermore, experience has shown that stove wiring, fan motors, vacuum motors and general laboratory equipment must be renewed constantly and at considerable expense due to the presence of these acidic gases. In addition, laboratory cleanliness is all but impossible to maintain given the presence of these gases, resulting in stained walls, floors and furniture. So extreme is the problem that to maintain laboratory cleanliness at even the most rudimentary level the walls must be recoated with paint after the production of each batch. Given these problems, FDA or regulatory authority inspection compliance has been problematic.

Beyond the difficulties associated with the production of known compositions, the known compositions have a variety of demonstrable shortcomings. First, prior compositions fail to produce an optimum effect in that they do not utilize the most effective administration methods or dosages. Second, known compositions are unsafe to manufacture in any significant quantity. Third, known compositions have a black, tarry appearance and are unappealing to the user in appearance. Fourth, known compositions are unappealing to the user in taste.

Accordingly, an improved formulation that demonstrates high antioxidant characteristics, increased efficacy against cancer, autoimmune diseases and a broad array of viruses (including the virus that causes AIDS) while allowing safe manufacture and appeal to the user is desired.

SUMMARY OF THE INVENTION

The present invention overcomes the failings of known compositions and methods of disease treatments as set forth in the prior art by providing a composition that is high in antioxidants, is safe to produce and is adaptable to administration to a patient without the undesirable appeal problems associated with the prior art and is more efficacious against disease states.

The composition of the present invention generally includes a salt of rhodizonic acid and an OH anion-generating base (resulting in croconic acid), a non-toxic acid, a quinone, a salt-containing sulfite, catechol and, optionally, an acetogenin. It may be characterized as a pharmaceutical, a nutraceutical, or a nutratherapeutical composition.

The composition of the present invention is a strong antioxidant. It is also effective against cancer, autoimmune diseases and viruses. The present composition has shown to be an effective antioxidant that works on all forms of the oxygen-related species of free radicals, including the peroxyl, hydroxyl and super oxide radicals. It is also believed that the composition of the present invention may have utility in reducing the side effects of radiation therapy and chemotherapy as well as in radio-sensitizing tumors, thus improving the efficacy of radiation therapy.

The composition of the present invention also overcomes the problems discussed above that are commonly associated with its production by the effective elimination of the noxious fumes. This results in improved laboratory conditions and ease of maintenance of proper conditions.

The present invention also improves the efficacy of the formula against tumors by providing chronic cytotoxic dosing of tumors and by providing a more consistent supply of antioxidants in the bloodstream, therefore providing a more effective in-vivo method of destroying the pernicious oxygen species of free radicals that are implicated in over 50 disease states.

As a further improvement over the art, the various compositions of the present invention achieve their efficacies without the use of such components as copper, potassium, triquinoyl, leuconic acid and rhodozonic acid. The absence of these components without compromising the effectiveness of the various compositions of the present invention is a testament to the unique approach taken herein. By avoiding such extra components both possible adverse patient reactions and cost may be reduced.

Other advantages and features of the present invention will become apparent from the following detailed description and appended claims.

DESCRIPTION OF THE DRAWINGS

FIG. 1 is a graph showing a comparison of the antioxidant effect of the formula of the present invention compared with antioxidants obtained from foods and pure vitamin sources.

FIG. 3 is a graph demonstrating pharmacokinetics of the levels of active ingredient after a single oral dose of the composition of the present invention.

FIG. 4 is a graph that shows the concentration and effect of the tumor-killing composition of the present invention over time.

FIG. 5 is a chart comparing the cytotoxicity of known anticancer pharmaceuticals and known nutraceuticals.

DETAILED DESCRIPTION OF THE PREFERRED EMBODIMENTS

Figure 2:
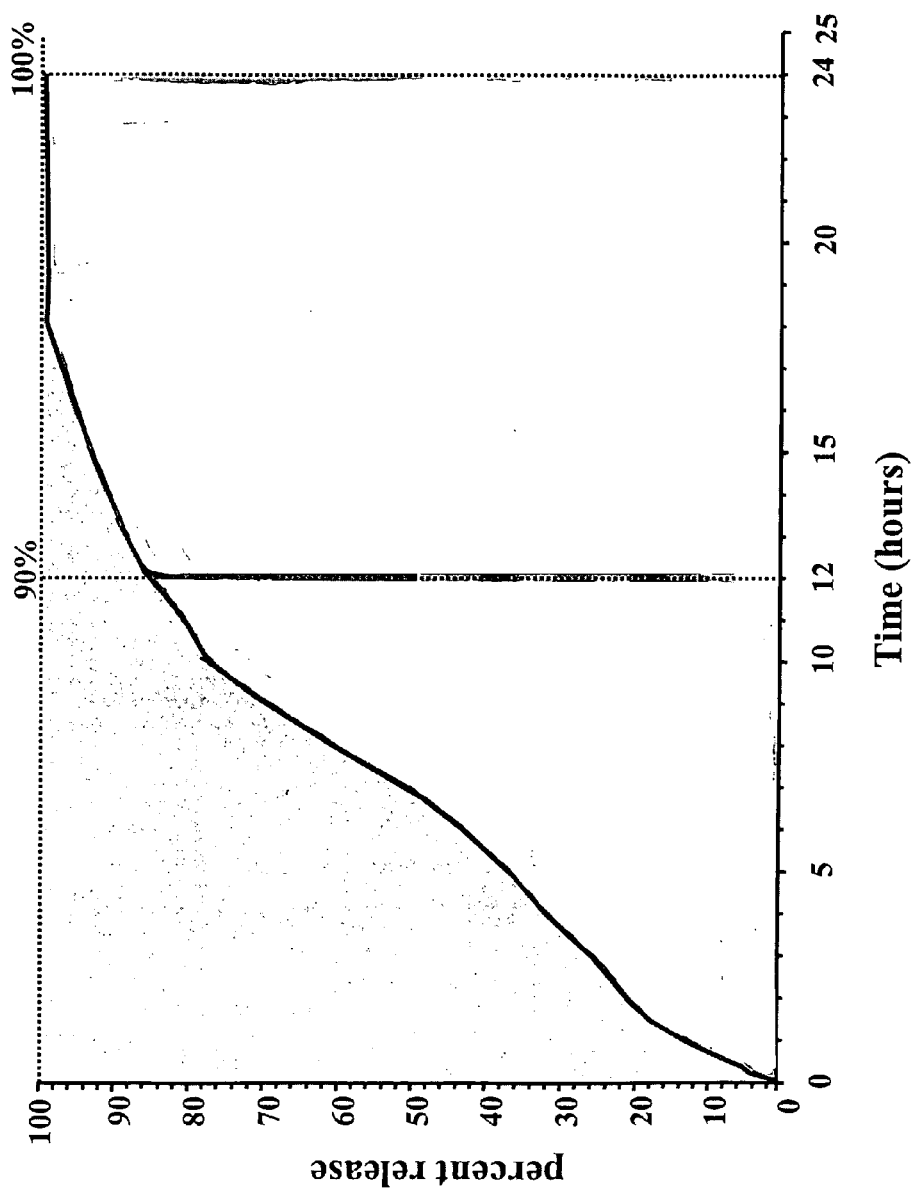
FIG. 2 is a graph illustrating the time release kinetics of the composition according to the present invention.

The composition and method of use of the present invention are set forth below. However, it is envisioned that alternate compositions of the present invention may be adopted without deviating from the present invention. The preferred embodiments are set forth hereafter.

The Composition

In general the composition consists of a salt of rhodizonic acid, an OH anion-generating base, a non-toxic acid, a quinone, a salt-containing sulfite, and catechol. An optional component is an acetogenin. The composition of the present invention provides significantly higher levels of antioxidants than the above-mentioned sources of vitamins E and C, broccoli, alpha-Lipoic acid, grapeseed and green tea extract, commonly accepted sources of antioxidants. The concentration of antioxidants of the present invention compared with these known sources is illustrated in FIG. 1 in which equivalent amounts of the natural sources are indicated compared with a single dose of the composition of the present invention.

Catechol, its Analogs and Equivalents

Catechol is a biologically significant organic phenol. It comprises two hydroxyl groups attached to a benzene ring. Catechol demonstrated significant anti-cancer activity in Applicant's studies. Catechol, its analogs and equivalents, as used herein may be characterized by the following:

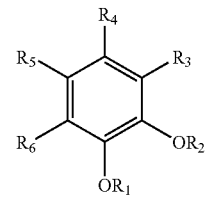

where $R_1$, $R_2$, $R_3$, $R_4$, $R_5$, $R_6$ may be any combination of hydrogen, alkyl, alkenyl hydroxyalkyl, carboxyl, aryl, alkenyl, cycloalkanes, cycloalkenes, glycine, glyco-saccharide, amino acid, peptide, polypeptide, protein and any of the foregoing attached to a central carbon, nitrogen, oxygen, sulfur, phosphorus or silicon atom. In addition, $R_1$, $R_2$, $R_3$, $R_4$, $R_5$, $R_6$ may be any of the R groups taken together will form a C3 to C10 membered ring.

As an antioxidant catechol may include flavone, flavonol, flavanone, isoflavone and anthocyane. Specifically, this may include flavone having the generic structure shown below (as a specific example luteolin is also illustrated):

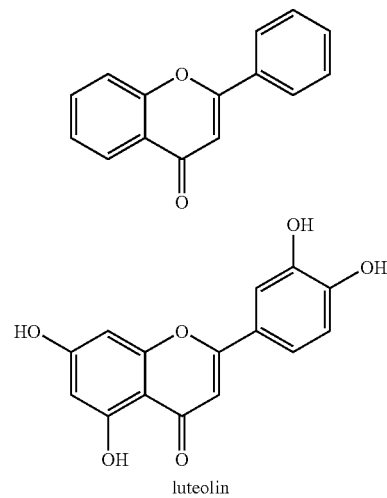

luteolin

As a flavonol it may have the generic structure shown below (as a specific example quercetin is also illustrated):

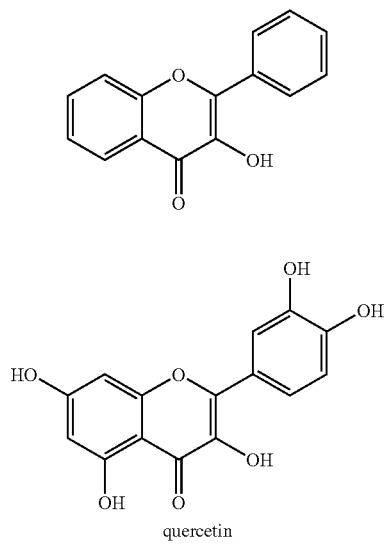
quercetin

As a flavanone it may have the generic structure shown below (as specific examples naringenin and taxifolin are also illustrated):

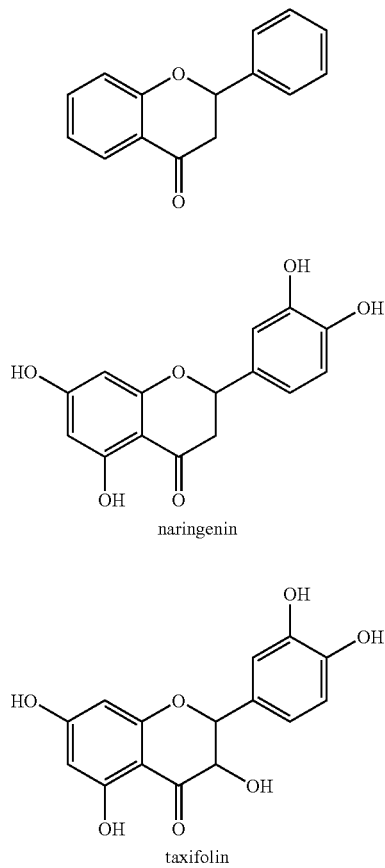
naringenin taxifolin

As an isoflavone it may have the generic structure shown below (as a specific example quercetin is also illustrated):

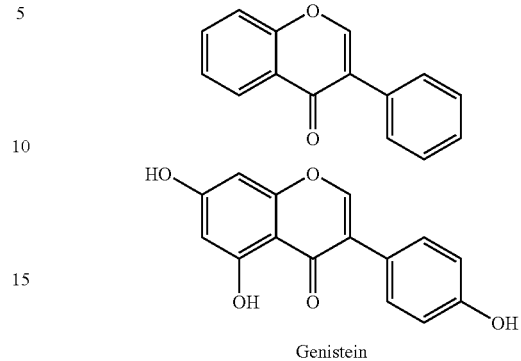
Genistein

Finally, as an anthocyane it may have the generic structure shown below (as a specific example cyanidin chloride is also illustrated):

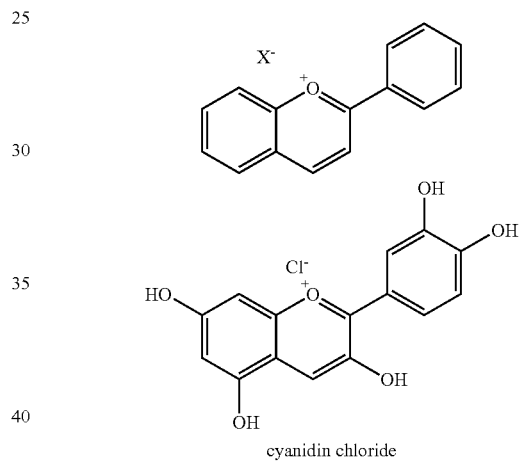
cyanidin chloride

Acetogenins

Acetogenins are active compounds which act as anti-neoplastic agents. It is believed that acetogenins act against cancer by regulating the production of ATP in the mitochondria of unhealthy cells. In some of its embodiments the present invention combines the powerful effect of acetogenins with catechol. The addition of acetogenins in the present composition improve the effectiveness of the catechol by destroying both resistant and non-resistant cells that otherwise might not be destroyed by catechol or acetogenin alone. This is important in that even a small number of cells left intact after treatment can multiply geometrically in little time and can render either catechol or acetogenin useless. Importantly, acetogenins kill multiple drug-resistant cells (MDR cells) which, in fact, may be resistant to catechol.

The Preferred Composition

The preferred composition of the present invention includes the following essential ingredients. Other ingredients (for example, flavorings) may be added without deviating from the scope of the present invention.

an antioxidant selected from the group consisting of catechol, its analogs and its equivalents in the amount of between 1 g and 10,000 g (10 kg), preferably between 150 g and 750 g an anti-neoplastic agent selected from the group consisting of acetogenin, its analogs and its equivalents in the amount of between 0.1 mg and 2,000 g (2 kg) and preferably between 80 grams and 100 grams an acid selected from the group consisting of croconic acid, its analogs and its equivalents and sulfites of croconic acid, their analogs and their equivalents in the amount of between 1 g and 1500 g (1.5 kg) and preferably between 15 g and 30 g a quinone selected from the group consisting of tetrahydroxyquinone, its analogs and its equivalents and sulfites of tetrahydroxyquinone, their analogs and their equivalents in the amount of between 1 g and 2,500 g (2.5 kg), preferably between 40 g and 80 g General Method for Making the Preferred Composition The composition of the present invention may be prepared by the following general procedures:

Step 1:

Create a suspension of a salt of rhodozonic acid ($C_6O_6Na_2$) and any base that can generate OH anions by mixing both in a flask with water. (It should be noted that analogs and equivalents of rhodozonic acid could be substituted for rhodozonic acid.) The amount of the water is preferably between 1 mL and 10,000 mL (10 L) and more preferably between 300 mL and 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg(OH)$_2$, and Ca(OH)$_2$. The amount of base is preferably between 1 g and 500 g and is more preferably between 100 g and 200 g.

Step 2:

Heat the suspension created in Step 1 to reflux until all of the rhodizonic acid is dissolved and the solution becomes bright yellow. The yellow color is indicative of the formation of croconic acid dipotassium salt ($C_5O_5K_2$, yield=20% by HPLC, 0.116 moles). Preferably the suspension is heated to between 25° C. and 100° C. More preferably the suspension is heated to between 90° C. and 100° C. The step of dissolving the rhodizonic acid takes about two hours. The new suspension demonstrates a pH of about 13.0.

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Bring the pH of the solution formed in Step 2 (or the solution formed in the Alternative Initial Step) to between preferably 7.0 and 10.0 and more preferably between 9.0 and 9.4.

Step 4:

Add tetrahydroxy-1,4-quinone ($C_6H_4O_6$) to the solution of Step 3, resulting in a black suspension. The tetrahydroxy-1,4-quinone is provided preferably in an amount of between 1 g and 2500 g (2.5 kg) and more preferably in an amount of between 40 g and 80 g. (Analogs and equivalents of tetrahydroxy-1,4-quinone may be substituted for tetrahydroxy-1,4-quinone.)

Step 5:

Add water and heat the suspension of Step 4 to completely dissolve all materials. Preferably between 1 mL and 2000 mL of water is used, and more preferably between 1000 mL and 1500 mL of water is used. Heating is preferably between 70° C. and 100° C. and is more preferably between 85° C. and 100° C. Dissolution of the materials preferably occurs between 1 and 180 minutes and more preferably occurs between 5 minutes and 60 minutes.

Step 6:

Dissolve a salt containing a sulfite ($SO_3^{-2}$) in water and add to the flask of the solution of Step 5. The salt used in Step 6 is preferably taken from the group consisting of $Na_2SO_3$, $Li_2SO_3$, $K_2SO_3$, $MgSO_3$, and $Ca_2SO_3$. The amount of sulfite used in this step is preferably between 1 g and 10,000 g (10 kg) and is more preferably between 1000 g (1 kg) and 3000 g (3 kg). The amount of water used in this step is preferably between 1 mL and 20,000 mL and more preferably is in the range of between 5000 mL and 7000 mL.

As an alternative to the addition of a salt containing a sulfite a sulfurous acid may be added to the base to generate sodium sulfite in situ.

Step 7:

Adjust the pH of the solution formed in Step 6 to preferably between 5.0 and 7.9 and more preferably to between 6.5 and 6.9.

Step 8:

Heat the mixture of Step 7 first to preferably between 60° C. and 100° C. and more preferably between 90° C. and 100° C. for preferably between 1 minute and 60 minutes and more preferably between 5 and 10 minutes.

Step 9:

Heat the mixture of Step 8 first to preferably between 0° C. and 100° C. and more preferably between 85° C. and 95° C. for preferably between 1 minute and 180 minutes and more preferably between 45 and 60 minutes. A black precipitate solution will form.

Step 10:

Allow the solution of Step 9 to cool to preferably between 0° C. and 60° C. and more preferably to between 20-25° C.

Step 11:

Dissolve between 1 g and 10,000 g (10 kg) and preferably between 150 g and 750 g of catechol ($C_6H_6O_2$) in water and add to the solution of Step 10. The amount of water used in this step is preferably between 1 mL and 5000 mL and more preferably is in the range of between 1000 mL and 2000 ml. (Analogs and equivalents of catechol may be substituted for catechol.)

Step 12:

Adjust the pH of the suspension of Step 11 to preferably between 1.0 and 12.0 and more preferably to between 7.0 and 7.5.

Step 13 (Optional):

An acetogenin (including its analogs and equivalents) may be added to the composition of Step 12 preferably in the amount of between 0.1 mg to 2000 g (2 kg) and, more preferably, in the amount of between 80 g and 100 g. The addition of an acetogenin would enhance the cancerous cell-killing potency of the composition, and particularly on drug-resistant (MDR) cells.

Step 14:

Increase the final volume of the solution of Step 12 (or optionally Step 13) by adding water preferably in the amount of between 5 L and 100 L and more preferably in the amount of between 10 L and 15L.

Additional Component—Time Release Mechanism

In vitro studies have verified that the above-mentioned Cantron® has anti-cancer activity. However, chronic dosing is required in order for this composition to be effective. The half-life of the Cantron® formula was thought, at one time, to be between six and eight hours. Importantly, recent studies undertaken by the inventor of the present composition and its method of formulation have shown, surprisingly, that the biomarker for Cantron® only stays in the bloodstream for a maximum of two hours and only stays in tumors for one hour.

According to the present invention, the delivery system has been altered by providing a time release formulation to obtain optimum anti-cancer effects by delivering a constant supply of the active ingredients into the bloodstream. It is this chronic exposure to tumors which obtains full efficacy of the present composition.

To effect a time release mechanism in the various compositions of the present invention, once the liquid material is produced as set forth above, the liquid is converted to a dry powder form by techniques such as lypholization, spray or by vacuum drying. The powder is then coated to produce time release beads or pellets. Capsules (gelatin or non-gelatin) are then filled with the beads or pellets. (The time release beads may be used in animal food such as animal treats as well.) A description of the time release process may be found in U.S. Pat. No. 5,292,461, "Process for the Production of Pellets."The time release formulation provides significant advantages over the prior art by sustaining an effective amount of the composition in the user's bloodstream at all times while medicated. Effectiveness of the time release formulation of the present composition is addressed below with respect to FIG. 2.

EXAMPLE

Method of Making the Preferred Composition

The following is a non-limiting example of a method of producing the preferred composition of the present invention.

A suspension of rhodizonic acid disodium salt ($C_6O_6Na_2$, 124 g, 0.58 moles) and KOH (2N, 168 g 1, 0.5 L, pH=12.4) was created by mixing the two components together in a 10 L flask. This suspension was heated for approximately two hours to reflux until all of the rhodizonic acid disodium salt was dissolved and the solution became bright yellow. HCL (2N, 200 ml) was then added to the solution to bring the pH of the solution formed to 9.2. (It should be noted that while an acid was added to the solution to adjust the pH to its desired level, it may be required in the alternative to use a base to make the same adjustment in a different experiment.) Tetrahydroxy-1,4-quinone ($C_6H_4O_6$, 50.4 g, 7.1 moles) was added to the solution to achieve a black suspension. Water was next added (1.3 L). The suspension was heated to 90° C. for 10 minutes to completely dissolve all of the materials. Sodium sulfite ($Na_2SO_3$, 1490 g, 11.8 moles) was dissolved in 6 L of water and was added to the 10 L flask of the solution. HCl was then added to bring the pH of the solution to 6.5-6.9.

The resulting mixture was heated first to 100° C. for 10 minutes and was then heated again to 90° C. for 50 minutes, resulting in the formation of a black precipitate solution. This solution was allowed to cool to room temperature (20-25° C.). An amount of Catechol ($C_6H_6O_2$, 365 g, 3.12 moles) was dissolved in 2 L of water. This was added to the solution. The pH of this suspension was adjusted to between 7.0-7.5. The final volume of the solution thus achieved was increased to 13 L by adding water.

Variants of the Preferred Composition

While the preferred composition has been set forth above, a number of variations of this composition have demonstrated characteristics that are similar to those of the preferred composition. These variants were prepared according to the following I. Variants with Catechol A. Catechol Plus Acetogenins Catechol ($C_6H_6O_2$) in the amount of between 1 g and 10,000 g (10 kg) and more preferably in the amount of between 150 g and 750 g is combined with an acetogenin preferably in the amount of between 0.1 mg and 2000 g (2 kg) and more preferably in the amount of between 80 g and 100 g. There are over 1000 different types of this compound plus extracts from source plants. This powder is then made into pill form or formulated as time release and made into pill form.

B. Catechol Plus THQ

Tetrahydroxy-1,4-quinone ($C_6H_4O_6$) preferably in the amount of between 1 g to 2500 g (2.5 kg) and more preferably between 40 g and 80 g is combined with catechol ($C_6H_6O_2$) preferably in the amount of between 1 g and 10,000 g (10 kg) and more preferably in the amount of between 150 g and 750 g. This powder is then made into pill form or formulated as time release and made into pill form.

C. Catechol Plus THQ Sulfite

Step 1:

Tetrahydroxy-1,4-quinone ($C_6H_4O_6$) preferably in the amount of between 1 g to 2500 g (2.5 kg) and more preferably between 40 g and 80 g is suspended in 3 liters of water and heated at 90° C. for 10 minutes to completely dissolve all materials.

Step 2:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 1.

Step 3:

Adjust the pH of the solution of Step 2 to 6.5-6.9.

Step 4:

Heat the mixture of Step 3 first (at sub-step (a)) to 100° C. for 10 minutes followed second by heating (at sub-step (b)) to 90° C. for 50 minutes.

Step 5:

Catechol (in ranges along the lines set forth above with respect to the preferred embodiment of the present invention) is added and the mixture is stirred to dissolve the catechol. This mixture was freeze dried to a powder and made into pill form or formulated as time release and made into pill form.

D. Catechol Plus Croconic Acid

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg (OH)$_2$, and Ca (OH)$_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt (C$_5$O$_5$K$_2$, yield=20% by HPLC).

Alternative Initial Step (Alternative to Steps 1 and 2):

Create a solution by adding between 1 g and 1500 g (1.5 kg) and preferably between 15 g and 30 g of croconic acid (C$_5$O$_5$K$_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Adjust the pH of the solution formed in Step 2 to 7.4 (6.9-7.9).

Step 4:

Catechol (in ranges along the lines set forth above with respect to the preferred embodiment of the present invention) was added and the mixture is stirred to dissolve catechol. This mixture was freeze dried to a powder and made into pill form or formulated as time release and made into pill form.

E. Catechol Plus Croconic Acid Sulfite

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg (OH)$_2$, and Ca (OH)$_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt (C$_5$O$_5$K$_2$, yield=20% by HPLC). (Note that as an alternative to forming croconic acid in the suspension croconic acid may be added directly. If this option is selected, preferably between 1 g and 1500 g (1.5 kg) and more preferably between 15 g and 30 g of croconic acid may be added preferably to between 1 mL and 10,000 mL of water and more preferably to between 300 mL and 1000 mL of water to form a solution.)

Alternative Initial Step (Alternative to Steps 1 and 2):

Create a solution by adding between 1 g and 1500 g (1.5 kg) and preferably between 15 g and 30 g of croconic acid (C$_5$O$_5$K$_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Adjust the pH of the solution formed in Step 2 to 9.2 (9.0-9.4).

Step 4:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 3.

Step 5:

Adjust the pH of the solution of Step 4 to 6.5-6.9.

Step 6:

Heat the mixture of Step 5 first (at sub-step (a)) to 100° C. for 10 minutes followed second by heating (at sub-step (b)) to 90° C. for 50 minutes.

Step 7:

Catechol (in ranges along the lines set forth above with respect to the preferred embodiment of the present invention) was added and the mixture was stirred to dissolve catechol. This mixture was freeze dried to a powder and made into pill form or formulated as time release and made into pill form.

II. Variants with Acetogenins

A. Acetogenin Plus THQ

Tetrahydroxy-1,4-quinone (C$_6$H$_4$O$_6$) preferably in the amount of between 1 g to 2500 g (2.5 kg) and more preferably between 40 g and 80 g is mixed with an acetogenin preferably in the amount of between 0.1 mg and 2000 g (2 kg) and more preferably in the amount of between 80 g and 100 g. The components were mixed as solids and were made into pill form or formulated as time release and made into pill form.

B. Acetogenin Plus THQ Sulfite

Step 1:

Tetrahydroxy-1,4-quinone (C$_6$H$_4$O$_6$) preferably in the amount of between 1 g to 2500 g (2.5 kg) and more preferably between 40 g and 80 g is suspended in 3 liters of water and heated at 90° C. for 10 minutes to completely dissolve all materials.

Step 2:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 1.

Step 3:

Adjust the pH of the solution of Step 2 to 6.5-6.9.

Step 4:

Heat the mixture of Step 3 first (at sub-step (a)) to 100° C. for 10 minutes followed second by heating (at sub-step (b)) to 90° C. for 50 minutes.

Step 5:

This solution is freeze dried to a powder.

Step 6:

An acetogenin, preferably in the amount of between 0.1 mg and 2000 g (2 kg) and more preferably in the amount of between 80 g and 100 g, is added to the powder in Step 5. The materials are then blended. This blended material is made into pill form or formulated as time release and made into pill form.

C. Acetogenin Plus Croconic Acid

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg $(OH)_2$, and Ca $(OH)_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Adjust the pH of the solution formed in Step 2 to 7.4 (6.9-7.9)

Step 4:

This solution is freeze dried to a powder.

Step 5:

An acetogenin in the amount of between 0.1 mg and 2000 g (2 kg) and more preferably in the amount of between 80 g and 100 g is added to the powder from Step 4. This mixture was made into pill form or formulated as time release and made into pill form.

D. Acetogenin Plus Croconic Acid Sulfite

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg $(OH)_2$, and Ca $(OH)_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Adjust the pH of the solution formed in Step 2 to 9.0-9.4.

Step 4:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 3.

Step 5:

Adjust the pH of the solution of Step 4 to 6.5-6.9.

Step 6:

Heat the mixture of Step 5 first (at sub-step (a)) to 100° C. for 10 minutes followed second by heating (at sub-step (b)) to 90° C. for 50 minutes.

Step 7:

The solution is freeze dried to a powder.

Step 8:

An acetogenin preferably in the amount of between 0.1 mg and 2000 g (2 kg) and more preferably in the amount of between 80 g and 100 g is added to the powder from Step 7. This mixture may be made into pill form or formulated as time release and made into pill form.

III. Variants with THQ

A. THQ Sulfite Plus Croconic Acid Sulfite

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL and 1000 mL (1 L). The amount of the rhodozonic acid is preferably between 1 g and 7300 g (7.3 kg) and is more preferably between 100 g and 150 g. The base is taken from the group consisting of KOH, LiOH, NaOH, Mg $(OH)_2$, and Ca $(OH)_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Step 3:

Adjust the pH of the solution formed in Step 2 to 9.0-9.4.

Step 4:

Tetrahydroxy-1,4-quinone ($C_6H_4O_6$) preferably in the amount of between 1 g to 2500 g (2.5 kg) and more preferably between 40 g and 80 g is suspended in the solution of Step 3, resulting in a black suspension.

Step 5:

Add water (1.3 L) and heat the suspension of Step 4 to 90° C. for 10 minutes to completely dissolve all materials.

Step 6:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 5.

Step 7:

Adjust the pH of the solution of Step 6 to 6.5-6.9.

Step 8:

Heat the mixture of Step 7 first (at sub-step (a)) to 100° C. for 10 minutes followed second by heating (at sub-step (b)) to 90° C. for 50 minutes, resulting in the formation of a black precipitate solution.

Step 9:

Allow the solution of Step 8 to cool to room temperature (20-25° C.).

Step 10:

Adjust the pH of the suspension of Step 10 to 7.0-7.5.

Step 11:

Increase the final volume of the solution of Step 10 to 13 L by adding the requisite amount of water. This mixture was freeze dried to a powder and made into pill form or formulated as time release and made into pill form.

C. THQ Plus Croconic Acid

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg$(OH)_2$, and Ca $(OH)_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Adjust the pH of the solution formed in Step 2 to 9.0-9.4.

Step 4:

Tetrahydroxy-1,4-quinone ($C_6H_4O_6$) preferably in the amount of between 1 g to 2500 g (2.5 kg) and more preferably between 40 g and 80 g is suspended in the solution of Step 3, resulting in a black suspension.

Step 5:

Add water (1.3 L) and heat the suspension of Step 4 to 90° C. for 10 minutes to completely dissolve all materials.

Step 6:

Allow the solution of Step 5 to cool to room temperature (20-25° C.).

Step 7:

Adjust the pH of the suspension of Step 6 to 7.0-7.5.

Step 8:

Increase the final volume of the solution of Step 7 to 13 L by adding the requisite amount of water. This mixture was freeze dried to a powder and made into pill form or formulated as time release and made into pill form.

Individual Component Compositions

Many of the positive effects may be delivered by treatment using individual components. Specifically, catechol (between 1 g-10,000 g), tetrahydroxyquinone (in its free and sulfited forms) (between 1 g-2500 g), and croconic acid (in its free and sulfited forms) (between 1 g-1500 g) may be individually delivered in the forms discussed herein, including both tablet (in both time release and non-time release forms), a powder, a gel capsule, an intravenous liquid, and transdermally.

Administration of the Composition

Regardless of the selected composition, the formulation of the present invention may be administered in any one of a variety of methods. A combination of these methods may also be used. These methods include liquid, powder or gel forms. The composition may be administered externally by transdermal delivery. Regardless of the form of the composition the objective is to achieve and maintain an effective amount of the composition in the patient's blood stream and at the tumor site. The forms of delivery discussed hereafter eliminate the negative appeal of the dark black liquid of earlier compositions while improving dosage compliance, optimum efficiency, and eliminate the staining of teeth and clothing that was an inherent characteristic of these earlier compositions.

Intravenous Administration

When administered in liquid form, the composition may be introduced via intravenous delivery. Intravenous administration particularly assures that an effective amount of the composition can be maintained in the patient's bloodstream at all times. As a further variant of the intravenous form of administration the composition of the present invention may be injected directly into the patient.

Oral Administration

When administered in liquid form, the composition may also be introduced orally. An optional approach for oral administration for the liquid composition is administrative by way of a gel capsule.

As set forth above, an alternative to the liquid form of the composition is to convert the liquid composition form to a dry powder form. The dry powder may then be tabletized and conveniently administered as a tablet (including sublinqual tablets) or may be coated with a time release agent then encapsulated as discussed above.

Oral forms of the composition of the present invention as described above should be taken every two hours during waking hours in either one or two tablets or capsules. The patient is given a double dose before retiring for the night. No more than six hours should elapse between doses.

Transdermal Administration

As an alternative to the intravenous and oral techniques for administering the composition of the present invention, the composition may be delivered transdermally by use of a patch or a transdermal gel. If administered as a patch, a single patch is attached to the patient's pulse point and is replaced every four to twelve hours. In either event, the transdermal delivery mechanism provides a constant supply of the active ingredients of the present invention to the patient's bloodstream.

Effectiveness of the Composition

The time-release kinetics of the composition of the present invention are set forth in FIG. 2 which shows percentage release along the Y-axis and time along the X-axis. As shown, release exceeds 90% after 12 hours. Release of 100% is achieved after 18 hours. FIG. 3 illustrates the levels of active ingredient after a single oral ingestion of of the present invention. Concentration is shown on the Y-axis and time (in hours) is shown on the X-axis.

In addition to its high-antioxidant concentration, the composition of the present invention has demonstrated significant anti-cancer effects. The composition provides a tumor-killing approach to resolution of a broad variety of cancers. The concentration of the tumor-killing composition over time is shown in FIG. 4. According to this graph, the surviving fraction of cancer cells (shown in the Y-axis) versus concentration (shown in the X-axis) is illustrated. The exposure is generally ineffective over two hours but begins to provide maximum effect over twenty-four hours. The concentration is clearly effective at seven days.

The composition of the present invention demonstrates high cytotoxicity when compared with anticancer pharmaceuticals and nutraceuticals. For colon cancer, the $IC_{50}$ values of 0.002, 0.005, 0.03, 0.10, and 0.15 are respectively set forth herein for the anticancer pharmaceuticals Taxol, Vincristine, Adriamycin, cis-Platinum and 5-Fluorouracil; and the $IC_{50}$ value of >100 is set forth herein for each of the neutraceuticals A-Lipoic Acid, Vitamin E, Vitamin C, Green Tea, and Grape seed.

The invention claimed is:

1. A composition for the treatment of colon cancer consisting essentially of therapeutically effective amounts of:
   an antioxidant having the form of

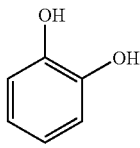

an acid selected from the group consisting of croconic acid and sulfites of croconic acid; and
   a quinone selected from the group consisting of tetrahydroxyquinone and sulfites of tetrahydroxyquinone; and
   an anti-neoplastic in the form of acetogenin.

2. The composition of claim 1 wherein the composition is prepared for administration to a patient in a form taken from the group consisting of a tablet, a capsule, a liquid in the form of a gel capsule, a liquid for intravenous administration, a transdermal patch, and a transdermal gel.

3. A composition for use as an oral medicament consisting essentially of therapeutically effective amounts of:
   an antioxidant having the form of

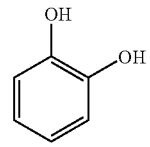

an acid selected from the group consisting of croconic acid and sulfites of croconic acid;
   a quinone selected from the group consisting of tetrahydroxyquinone and sulfites of tetrahydroxyquinone; and
   an anti-neoplastic in the form of acetogenin.

4. The composition of claim 3 wherein the composition is prepared for administration to a patient in a form taken from the group consisting of a tablet, a capsule, a liquid in the form of a gel capsule, a liquid for intravenous administration, a transdermal patch, and a transdermal gel.

5. A composition to quench the oxygen related species of free radicals consisting essentially of therapeutically effective amounts of:
   an antioxidant having the form of

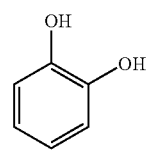

an acid selected from the group consisting of croconic acid and sulfites of croconic acid;
   a quinone selected from the group consisting of tetrahydroxyquinone and sulfites of tetrahydroxyquinone; and
   an anti-neoplastic in the form of acetogenin.

6. The composition of claim 1 wherein the composition is prepared for administration to a patient in a form taken from the group consisting of a tablet, a capsule, a liquid in the form of a gel capsule, a liquid for intravenous administration, a transdermal patch, and a transdermal gel.

* * * * *